(12) United States Patent
Lu et al.

(10) Patent No.: US 10,418,549 B2
(45) Date of Patent: Sep. 17, 2019

(54) METHOD FOR EVALUATING THERMAL EFFECT AND REDUCING THERMAL CROSSTALK OF THREE-DIMENSIONAL INTEGRATED RESISTIVE SWITCHING MEMORY

(71) Applicant: Institute of Microelectronics, Chinese Academy of Sciences, Chaoyang District, Beijing (CN)

(72) Inventors: Nianduan Lu, Beijing (CN); Pengxiao Sun, Beijing (CN); Ling Li, Beijing (CN); Ming Liu, Beijing (CN); Qi Liu, Beijing (CN); Hangbing Lv, Beijing (CN); Shibing Long, Beijing (CN)

(73) Assignee: INSTITUTE OF MICROELECTRONICS, CHINESE ACADEMY OF SCIENCES, Chaoyang District, Beijing (CN)

( * ) Notice: Subject to any disclaimer, the term of this patent is extended or adjusted under 35 U.S.C. 154(b) by 0 days.

(21) Appl. No.: 16/064,116

(22) PCT Filed: Aug. 12, 2016

(86) PCT No.: PCT/CN2016/094862
§ 371 (c)(1),
(2) Date: Jun. 20, 2018

(87) PCT Pub. No.: WO2017/107504
PCT Pub. Date: Jun. 29, 2017

(65) Prior Publication Data
US 2018/0366643 A1    Dec. 20, 2018

(30) Foreign Application Priority Data
Dec. 24, 2015    (CN) .......................... 2015 1 0983042

(51) Int. Cl.
*H01L 45/00*    (2006.01)
*G01N 25/20*    (2006.01)
(Continued)

(52) U.S. Cl.
CPC ............. *H01L 45/04* (2013.01); *G01N 25/20* (2013.01); *G11C 7/04* (2013.01); *G11C 13/0002* (2013.01);
(Continued)

(58) Field of Classification Search
CPC ............... H01L 45/1293; H01L 45/128; H01L 45/1233; H01L 45/04; H01L 45/00;
(Continued)

(56) References Cited

U.S. PATENT DOCUMENTS 8,141,020 B2 * 3/2012 Emma ................. G06F 17/5072
716/118
9,323,870 B2 * 4/2016 Chandra ................ G06F 17/50
(Continued)

FOREIGN PATENT DOCUMENTS

| CN | 101452891 | 6/2009 |
| CN | 103247755 | 8/2013 |
| TW | 201424070 | 6/2014 |

OTHER PUBLICATIONS

International Search Report and Written Opinion for Application No. PCT/CN2016/094862, dated Oct. 10, 2016.
(Continued)

*Primary Examiner* — Vanthu T Nguyen
(74) *Attorney, Agent, or Firm* — K&L Gates LLP

(57) ABSTRACT

A method for evaluating the thermal effects of 3D RRAM arrays and reducing thermal crosstalk, including the following steps: Step 1: calculating the temperature distribution in the array through 3D Fourier heat conduction equation; Step 2, selecting a heat transfer mode; Step 3, selecting an
(Continued)

appropriate array structure; Step 4, analyzing the effect of position of programming device in the array on the temperature; Step 5, analyzing the thermal crosstalk effect in the array; Step 6, evaluating thermal effects and thermal crosstalk; Step 7, changing the array structure or modify operating parameters based on the evaluation results to reduce the thermal crosstalk. According to the method of the present invention, the influence of the position of the device on the temperature is analyzed according to the heat transfer mode of the 3D RRAM array, the thermal effect and the thermal crosstalk are evaluated, and the appropriate array structure and operating parameters are selected according to the evaluation result, which effectively improves the thermal stability of the device.

7 Claims, 4 Drawing Sheets

(51) Int. Cl.
      *G11C 13/00*       (2006.01)
      *H01L 27/24*       (2006.01)
      *G11C 7/04*       (2006.01)

(52) U.S. Cl.
    CPC ...... *H01L 27/2409* (2013.01); *H01L 27/2481* (2013.01); *H01L 45/00* (2013.01); *H01L 45/128* (2013.01); *H01L 45/1233* (2013.01); *H01L 45/1293* (2013.01); *G11C 2213/71* (2013.01); *G11C 2213/72* (2013.01)

(58) Field of Classification Search
    CPC ............. H01L 27/2481; H01L 27/2409; G11C 2213/71; G11C 2213/72; G11C 13/0002; G11C 7/04; G01N 25/20
    See application file for complete search history.

(56) References Cited

U.S. PATENT DOCUMENTS

| | | | | |
|---|---|---|---|---|
| 9,582,621 | B2* | 2/2017 | Anderson | ........... G06F 17/5036 |
| 2013/0285739 | A1* | 10/2013 | Blaquiere | ...... G01R 31/318555 |
| | | | | 327/565 |
| 2014/0061576 | A1 | 3/2014 | Toh et al. | |

OTHER PUBLICATIONS

International Search Report for Application No. PCT/CN2016/094862, dated Oct. 10, 2016.

Sun, Pengxiao et al., "Physical model of dynamic Joule heating effect for reset process in conductive-bridge random access memory", Journal of Compitational Electronics, vol. 2, No. 13, Jan. 1, 2014 (Jan. 1, 2014), ISSN: 1572-8137, pp. 432-434.

* cited by examiner

METHOD FOR EVALUATING THERMAL EFFECT AND REDUCING THERMAL CROSSTALK OF THREE-DIMENSIONAL INTEGRATED RESISTIVE SWITCHING MEMORY

CROSS-REFERENCE TO RELATED APPLICATIONS

This application is a U.S. National Stage Entry under 35 U.S.C. § 371 of International Patent Application No. PCT/CN2016/094862, titled METHOD FOR EVALUATING THERMAL EFFECT AND REDUCING THERMAL CROSSTALK OF THREE-DIMENSIONAL INTEGRATED RESISTIVE SWITCHING MEMORY, filed Aug. 12, 2016, which application claims priority under 35 U.S.C. 119(b) and 37 CFR 1.55 to Chinese Application No. 201510983042.6, filed Dec. 24, 2015, the entire disclosures of which are incorporated by reference herein.

TECHNICAL FIELD

This invention belongs to the field of microelectronic devices and memory technologies, particularly relates to a device structure of a three-dimensional integrated resistive switching memory, and a method for evaluating thermal effect and reducing thermal crosstalk thereof.

BACKGROUND TECHNIQUE

Resistive switching memory (RRAM) is based on the fact that the resistance of its material can be reversibly switched between high and low resistance states. There are mainly two basic structures: metal-insulator-semiconductor (M-I-S) and metal-insulator-metal (M-I-M). Resistive switching memory has been widely used in the industry and paid extensive attention in academia due to its simple structure, good compatibility with conventional CMOS processes, low set current, low power consumption, compatibility with logic processes, and the ability of mass storage of three-dimensional (3D) stacks. Many research institutes and companies have invested in relating research. In order to meet the requirements of greater data storage density and faster access to information, the current international orientation for the future development of RRAM is ultra-high-density storage. The 3D integration technology is the inevitable choice for ultra-high-density storage.

The three-dimensional resistive switching memory crossbar array is one of the most competitive candidates for future non-volatile memory integration technologies. In order to compete against the three-dimensional NAND flash memory with ultra-high integration density, it is necessary to deeply understand various physical effects in the operation process. In general, in the three-dimensional integration of RRAM devices, a selective device unit is required in series on the RRAM device to suppress the leakage current in the array integration. The 1D1R structure (D: represents a diode and R represents a resistive switching device) has great potential for application in 3D integrated arrays due to its simple program/erase operations and easy fabrication. A 1D1R type resistive switching memory cell generally has unipolar resistive switching characteristics (i.e., set and reset operations are at the same voltage polarity), and its reset process is dominated by Joule heating effect. In order to promote the practical use of the 1D1R three-dimensional integrated array, it is necessary to conduct detailed studies on the thermal conductivity and conductance effects of the device. Since the word/bit lines generally have extremely high thermal conductivity in the array integration, the thermal crosstalk effect is one of the key issues to be considered in the integration of three-dimensional cross arrays of RRAM devices.

There have already been many reports on the Joule heating effect of RRAM devices, but all of current works are at the level of a single RRAM device, not considering diode selective device in array integration yet. In addition, due to the difficulty of experimentally measuring the thermal effects during the 3D integration of resistive switching memories, the conventional thermal analysis methods are difficult to perform. Therefore, there are few reports on the thermal effects and thermal crosstalk of three-dimensional resistive switching memories, and the relevant technical measures have yet to be further resolved.

SUMMARY OF THE INVENTION

From the foregoing, the purpose of the present invention is to provide a method for evaluating the thermal effect and improving the thermal crosstalk of three-dimensional integrated resistive switching memory corresponding to the shortcomings of current three-dimensional integrated resistive switching memory.

To this end, the present invention provides a method for evaluating the thermal effects of 3D RRAM arrays and reducing thermal crosstalk which includes the following steps:

Step 1, calculating the temperature distribution in the array through 3D Fourier heat conduction equation;
Step 2, selecting a heat transfer mode;
Step 3, selecting an appropriate array structure;
Step 4, analyzing the effect of position of programming device in the array on the temperature;
Step 5, analyzing the thermal crosstalk effect in the array;
Step 6, evaluating thermal effects and thermal crosstalk;
Step 7, changing the array structure or modifying operating parameters to reduce the thermal crosstalk based on the evaluation results.

Among them, the 3D Fourier heat conduction equation in step 1 is $$\nabla k_{th} \nabla T + \sigma |\nabla V|^2 - c\rho \frac{\partial T}{\partial t} = 0 \qquad (1)$$

wherein $k_{th}$ represents thermal conductivity, T represents temperature, c represents heat capacity, $\rho$ represents mass density of the material, t represents time, and $\sigma$ represents electric conductance of the material; preferably, the electric conductance of material changes with temperature, as shown in the following formula (2):

$$\sigma = \frac{\sigma_0}{1 + \alpha(T - T_0)} \qquad (2)$$

wherein $\alpha$ represents temperature coefficient of resistance, $\sigma_0$ represents the resistivity at room temperature $T_0$; further preferably, the word line (WL) or bit line (BL) at the top and bottom of the array has an ideal heat dissipation package structure, the temperatures of top and bottom of the array are kept at room temperature $T_0$ in the calculation, as shown in equation (3):

$$T - T_0 |_{BC} = 0. \qquad (3)$$

Among them, in the heat transfer mode:
(i) heat is transferred between devices of same layer through the isolating dielectric material, or
(ii) heat is transferred between RRAM devices of different layer in vertical direction.

Among them, the array structure is a 3D array of device units, each of which consists of one RRAM and one diode, wherein
(i) the RRAM in one unit is connected to the diode in the adjacent unit via a WL/BL, or
(ii) the diode in one unit is connected to the diode in the adjacent unit via a WL/BL.

Wherein in step 5, the thermal effect of the 3D integrated resistive switching device is analyzed by using the formula described in step 1 based on the physical parameters of conductive filaments of the RRAM device, diodes, and WL/BL, wherein the physical parameters are selected from any one of the following or any combinations thereof: radius, thickness, thermal conductivity, heat capacity, reference conductivity at room temperature, width, reset voltage, and room temperature.

Wherein in step 6 the thermal effects and thermal crosstalk in the device are estimated using transient temperature based on the Arrhenius law of the memory device.

Wherein step 7 comprises: reducing the reset current or adopting a cycle-rehabilitate technique; preferably, the cycle-rehabilitate technique comprises after cr times cycles of RRAM arrays, all of the low resistance state devices in the array are erased and then a reprogramming operation is performed; further preferably, it is guaranteed that the resistance value can still distinguish between high and low resistance states in the degraded crosstalked RRAM device after cr times operations.

According to the method of the present invention, the influence of the position of the device on the temperature is analyzed according to the heat transfer mode of the 3D RRAM array, the thermal effect and the thermal crosstalk are evaluated, and the appropriate array structure and operating parameters are selected according to the evaluation result, which effectively improves the thermal stability of the device.

DESCRIPTION OF THE DRAWINGS

Hereinafter, the technical solution of the present invention will be described in detail with reference to the accompanying drawings, in which:

FIG. 2 shows a schematic diagram of a possible three-dimensional integrated resistive switching memory device, wherein
FIG. 2(a) shows a crossbar array structure in which a resistive switching memory cell is connected to a diode via a bit line/word line (WL/BL),
FIG. 2(b) shows a crossbar array structure in which a diode is connected to a diode via a bit line/word line (WL/BL), and
FIG. 2(c) shows a 1D1R structure (D represents a diode, R represents a resistive switching memory unit) in which a single device unit is composed of a resistive switching memory (RRAM) cell and a diode (Diode) in series.

FIGS. 5(d), 5(e) and 5(f) depict the temperature distribution of systems for the different programming times shown in FIGS. 5(a), 5(b) and 5(c), respectively.

DETAILED DESCRIPTION

Figure 1:
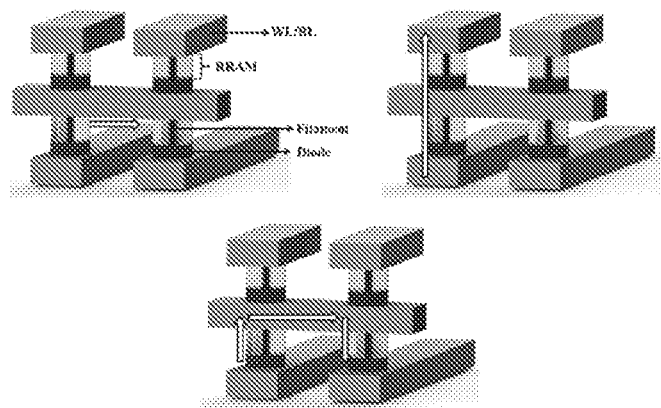
FIG. 1 shows a schematic diagram of possible heat conduction paths (white arrows) in the three-dimensional integrated crossbar array provided by the present invention.

The features and technical effects of the technical solution of the present invention are described in detail below with reference to the accompanying drawings and exemplary embodiments. A method for effectively reducing the thermal crosstalk effect of a 3D RRAM array is disclosed. It should be noted that like reference numerals refer to similar structures, and the terms "first", "second", "upper", "lower" and the like used herein may be used to modify various device structures or manufacturing processes. Such modifications, unless specified, do not imply a spatial, order or hierarchical relationship between the structure of the modified device or the manufacturing process.

The method includes the following steps:

Step 1: Calculating the Temperature Distribution in the Integrated Array Via Three-Dimensional Fourier Heat Conduction Equation The temperature distribution in the RRAM three-dimensional integrated array can be described using various heat conduction models and their corresponding equations, but based on the accuracy considerations, the three-dimensional Fourier heat conduction equation shown in equation (1) is optimally described:

$$\nabla k_{th} \nabla T + \sigma |\nabla V|^2 - c\rho \frac{\partial T}{\partial t} = 0 \quad (1)$$

In equation (1), $k_{th}$ denotes thermal conduction, T denotes temperature, c denotes heat capacity, ρ denotes mass density of the material, t denotes time, and σ denotes conductance of the material. The conductivity of the material will generally change with temperature and can be expressed as formula (2), $$\sigma = \frac{\sigma_0}{1 + \alpha(T - T_0)}, \quad (2)$$

In equation (2), α denotes temperature coefficient of resistance, and $\sigma_0$ denotes resistivity at room temperature $T_0$. The word line (WL) or bit line (BL) at top and bottom of the array is assumed to have an ideal heat dissipation package structure, and the room temperature is maintained at $T_0$ during calculation as shown in formula (3):

$$T - T_0 |_{BC} = 0 \quad (3)$$

In order to accurately calculate the temperature effect of the device in the present invention, a three-dimensional resistance network model is used in conductance simulation, and the calculation theory is based on Ohm's law and Kirchhoffs equation.

It is often difficult to accurately calculate the heat distribution of the entire device array, but some of the characterization areas (specific device structures) in the array may be selected for the local area of the array (e.g., test structures fabricated in dummy cells on the wafer). The follow-up process will be corrected according to the relationship between certain test measured data (local area temperature or thermal imaging line, etc.) and the theoretical calculation data, for example, the actual array structure of the future design will be changed and corrected through test data feedback to improve accuracy.

Step 2: Considering the Heat Transfer Mode in 3D Integrated Resistive Devices

FIG. 1 shows several possible thermal conduction paths (shown by white arrows) in a three-dimensional integrated RRAM crossbar array. After an individual RRAM device generates heat, the heat can be transferred among devices in the same layer through the isolating dielectric material, and can also be transferred among RRAM devices in different layers in the vertical direction or between adjacent cells. In addition, the W/B lines of the RRAM device generally have a high thermal conductivity and significant thermal conduction as well. Specifically, a suitable heat transfer mode and corresponding RRAM and diode stack structures should be set (that is, selected in the next batch of RRAM array manufacturing) by analyzing the device structure especially based on the heat distribution corresponding to different heat transfer modes and the subsequent corresponding thermal crosstalk influences.

Step 3: Selecting the Appropriate 3D Integrated Array

The corresponding heat distribution of the current device (RRAM array) is calculated (or simulated) according to the heat transfer model, and the appropriate array structure is selected for subsequent thermal crosstalk evaluation. And the array structure design in next batch of product can be modified in follow-up based on the assessment results and feedback.

Figure 2:
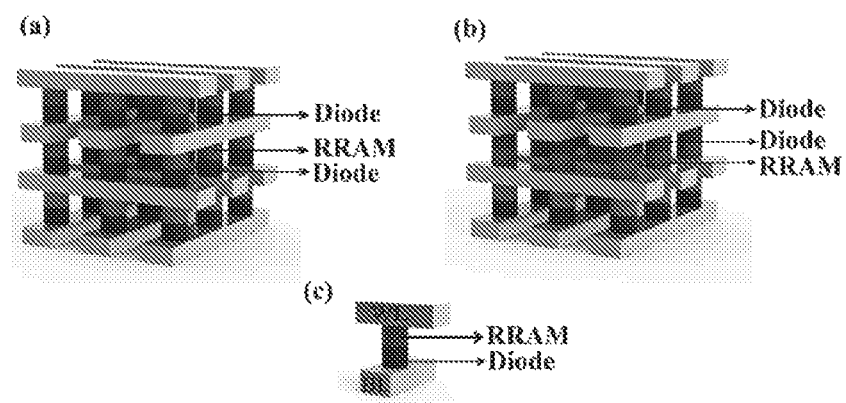

Specifically, a schematic diagram of possible device structures is selected. One is a crossbar array structure in which a resistive switching memory cell is connected to a diode via a word line/bit line (WL/BL) (as shown in FIG. 2(a)), another is a crossbar array structure in which a diode is connected to a diode via a WL/BL (as shown in FIG. 2(b)). A single device unit is composed of a resistive switching memory (RRAM) cell and a diode (Diode) in series, for example 1D1R as shown in FIG. 2(c) (D represents a diode, R represents a resistive switching memory unit).

Step 4: Analyzing the Effect of Programming Device's Position in 3D Integrated Resistive Device on Temperature Based on the heat conduction paths shown in step 2, the heat distribution of the three-dimensional integrated resistive device can be calculated by combining with the formula in step 1. When the programming device is closer to the top or bottom boundary, the generated heat is easily led off, so the final temperature is lower; when the programming device is in the middle layer, the generated heat is hard to pass out, so the corresponding temperature is relatively higher. Here only the position of the working device is shown. If other positions in middle portion are also in working mode, the heat conduction fashion is mainly based on the three forms of FIG. 1, which affect the heat transfer from other devices. There is a certain relationship between temperature and device's height/path length to the top or bottom. Although it is difficult to use a specific functional relationship (that is, give out a complete equation), it is possible to fit via a number of experimental tests and theoretical calculations on local structures.

Figure 5:
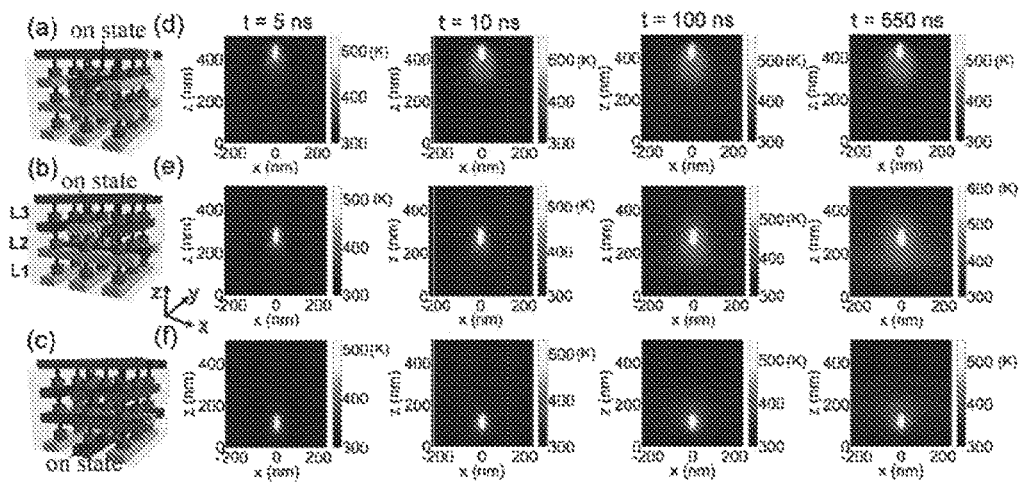
FIG. 5 shows temperature maps in a 3×3×3 array in the present invention, wherein FIG. 5(a), FIG. 5(b), and FIG. 5(c) respectively a programming operation on the RRAM devices in the first layer, the second layer, and the third layer, wherein the programming device is connected to the green diode unit (conducting state).
Figure 6:
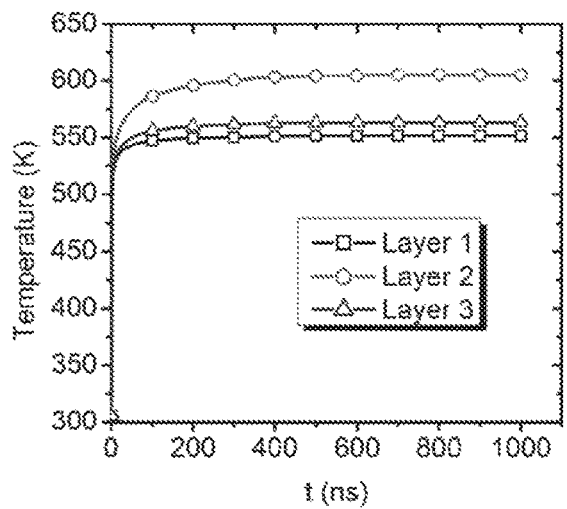
FIG. 6 shows the change of maximum temperature of a programming RRAM device in the present invention overtime, wherein Layer 1-3 corresponds to FIG. 5(a)-(c) respectively.

The calculated thermal effects of the three-dimensional integrated resistive switching memory are shown in FIG. 5 and FIG. 6. FIG. 5 shows the change of temperature distribution of the system (FIGS. 5d, 5(e) and 5(f) are respectively the temperature distribution of system for different programming time shown in FIGS. 5(a), 5(b) and 5(c)) when the programming device is at different layers of the integrated array (shown as in FIGS. 5(a), 5(b) and 5(c)). FIG. 6 shows the change of maximum temperature of a programming RRAM device over time. It can be seen that different positions of the programming device result in quite large temperature variation (the maximum temperature difference is about 50K). So, when the programming device is closer to the top or bottom boundary, the generated heat is easily led off (as described in the model description section, assuming that the integrated array has ideal package heat dissipation conditions, and the upper and lower boundaries maintain at room temperature), so the final temperature is relatively lower. When the programming device is in the middle layer, the generated heat is hard to pass out, so the corresponding temperature is relatively higher. In the present invention, only the 3×3×3 layers stack integration is discussed. In high-density 3D integration, the number of stacked layers in the vertical direction can reach scores of layers, this temperature difference will be more apparent.

Figure 3:
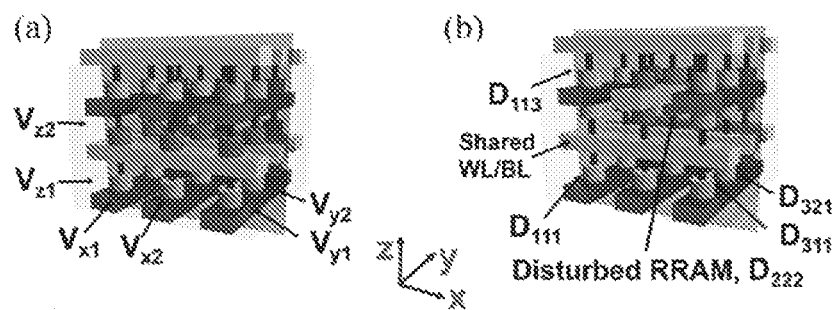
FIG. 3 shows two "worst cases" schematic diagrams for calculating the thermal effects of the three-dimensional integrated resistive switching memory device of the present invention, wherein the crosstalked device (reference number D222) is at the center of the array and is surrounded by other programming devices.

Step 5: Analyzing Thermal Crosstalk Effects in 3D Integrated Resistive Switching Devices In 3D integrated resistive switching devices, due to the high thermal conductivity of the word/bit lines, Joule heat is generated during the reset of the programmed device, the temperature rises accordingly, and the temperature of the un-programmed devices around it also passively increases. This is the so-called thermal crosstalk phenomenon. Thermal crosstalk can degrade the resistive state holding characteristics of the crosstalked devices. In order to study the influence of the thermal crosstalk phenomenon on device performance, the present invention adopts a programming model as shown in FIG. 3: that is, a plurality of RRAM devices are under programming operation simultaneously. In this programming mode, the programmed devices have a strongest thermal crosstalk effect on the resistive switching devices that are surrounded by them.

The structure of FIG. 3(a) is selected to create a 3×3×3 crossbar RRAM. The feature size of the device is 200 nm to 30 nm. Then the formula and methods described in Step 1 are used to analyze the thermal effects of three-dimensional integrated resistive switching devices together with the basic physical parameters listed in Table 1. Among them, it is worthy of special attention that the device size plays an important role in the temperature distribution. For example, a decrease in the device size leads to a significant change in the temperature distribution (e.g., increase, quadricly or cubicly increase, exponential increase, etc.).

Figure 4:
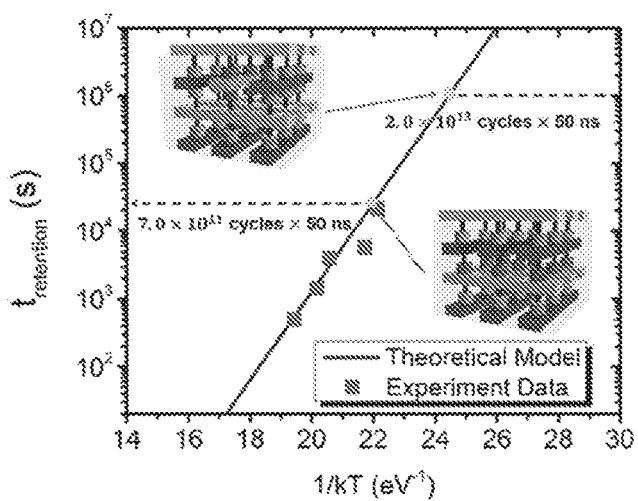
FIG. 4 shows the Arrhenius plot of the low-resistance retention properties of the RRAM tested in the present invention (the device being tested is a Ni filament type resistive switching device) and the evaluation of the retention performance of the crosstalked RRAM device in the case of thermal crosstalk.

Therefore, the two low-resistance retention time $t_{retention}$ calculated in FIG. 4 correspond to $t_{retention}/(t_{reset}-50 \text{ ns})$, ie, $7.0 \times 10^{11}$ and $2.0 \times 10^{13}$ successive program/erase operations (either is a reasonable number of cycles for the RRAM device), during which time the crosstalked RRAM device is kept being not programmed.

In other words, thermal crosstalk can affect the low-resistance retention characteristics of the device being crosstalked. After $7.0 \times 10^{11}$ and $2.0 \times 10^{13}$ successive program/erase operations, the low-resistance crosstalked RRAM device will be changed into a high-impedance state due to the thermal crosstalk effect failures. Since the current is very small during the Set process, the corresponding Joule heating effect can be negligible.

In order to study the influence of the thermal crosstalk phenomenon on device performance, the present invention selects two "worst cases" as shown in FIG. 3:—that is, a plurality of RRAM devices are programmed at the same time, so the crosstalk effect is strongest on the surrounded

TABLE 1

Physical parameters used in the simulation

| parameter | value | parameter | value | parameter | value |
|---|---|---|---|---|---|
| $r_{cf}$ | 8 nm | $r_{diode}$ | 40 nm | $h_{line}$ | 30 nm |
| $h_{cf}$ | 80 nm | $h_{diode}$ | 50 nm | $k_{th\_diode}$ | 22 W/(m K) |
| $k_{th\_cf}$ | 22 W/(m K) | $k_{th\_diode}$ | 11.7 & 2 W/(m K) | $c_{line}$ | 445 J/(kg K) |
| $c_{cf}$ | 445 J/(kg K) | $c_{diode}$ | 710 J/(kg K) | $\sigma_{0\_line}$ | $1.23 \times 10^5$ S/m |
| $\sigma_{0cf}$ | $1.23 \times 10^5$ S/m | $\sigma_{0\_diode}$ | $3.07 \times 10^3$ & $5 \times 10^{-2}$ S/m | $\rho_{line}$ | $8.9 \times 10^3$ Kgm$^{-3}$ |
| $\alpha_{cf}$ | 0.0014 | $\rho_{diode}$ | $4.17 \times 10^3$ Kg m$^{-3}$ | $V_{b)}$ | 1.2 V |
| $\rho_{cf}$ | $8.9 \times 10^3$ Kg m$^{-3}$ | $w_{line}$ | 100 nm | $T_0$ | 300 K |

In the table, r denotes radius, h denotes thickness, $k_{th}$ denotes thermal conductivity, c denotes heat capacity, $\sigma_0$ denotes reference conductivity at room temperature, w denotes width, subscript cf, diode and line represent conductive filaments (CF), diode and wordline/bitline (WL/BL) cells respectively. V denotes the reset voltage and $T_0$ denotes room temperature. In Table 1, $k_{th\_diode}$ and $\sigma_{0\_diode}$ give two values respectively corresponding to the values in the diode forward conduction state and the reverse shutdown state.

Step 6: Evaluating Thermal Effects and Thermal Crosstalk

Since it takes a long time for a device in a three-dimensional integrated RRAM array to reach a thermal stable state, which exceeds the reset time of a general RRAM device, the present invention uses the transient temperature to measure the effect of thermal effects and thermal crosstalk in the device.

This method is based on Arrhenius' law of memory devices. The method is to assume the reset time $t_{reset}=100$ ns for an individual 1D1R cell. When t=50 ns, the maximum temperature $T_p$ in the crosstalked device in the three-dimensional integrated RRAM is 523K and 474K, as shown in FIG. 4. The temperature can be transformed into the corresponding retention time $t_{retention}$ ($t_{retention} \propto e^{(qEa/kTp)}$) by Arrhenius's law, where q is the unit charge, $E_a$ is activation energy, k is Boltzmann's constant, and $T_p$ is temperature. Therefore, it can be deduced that $t_{retention}$ is $3.5 \times 10^4$ s and $1.0 \times 10^6$ s under the conditions with temperature $T_p=523K$ and $T_p=474K$. The heat generated by the programmed device is passed to the crosstalked low-resistance device. It is assumed that the uninterrupted program/erase operation is equivalent to the continuous heating on the crosstalked RRAM device at a constant temperature $T_p$, and the effective heating time in each program/erase operation is $t_{reset}-50$ ns.

resistive switching device. In order to implement the parallel program/erase operations in RRAM devices in different layers, a Shared WL/BL is introduced into the three-dimensional integrated RRAM crossbar structure, as shown in FIG. 3(b). The RRAM device in a programmed operation in the figure is connected to a dark-colored diode cell, and the device in an unprogrammed operation is connected to a light-colored diode. Different WL/BL colors can be distinguished for corresponding voltage application way (light color lines are applied by voltage V, darker lines are grounded).

Figure 7:
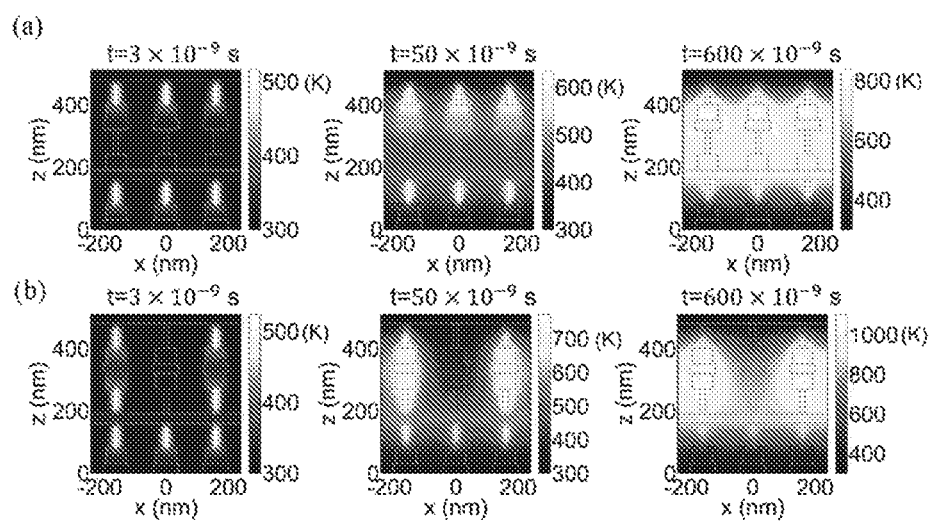
FIG. 7 shows the change of temperature distribution obtained by two different programming methods in the present invention over time, wherein the crosstalked device (reference number D222) is at the center position of the array and is surrounded by other programming devices, the voltage is applied on the electrode connected to the RRAM device unit during reset operation, keeping the other electrode grounded.
Figure 8:
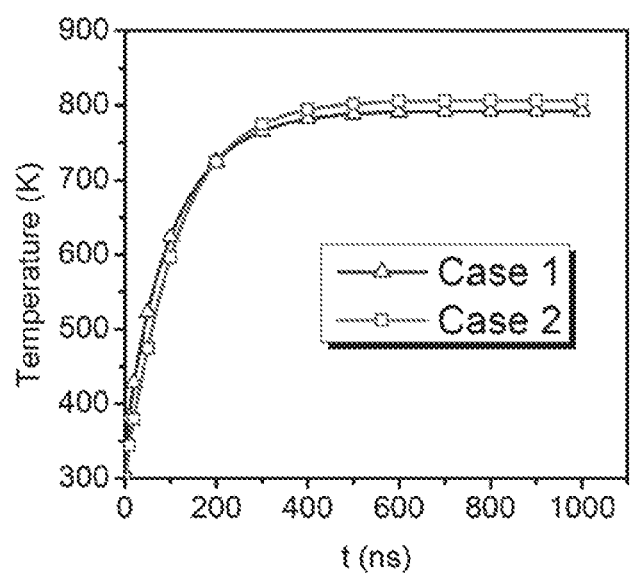
FIG. 8 shows simulation results of the change of maximum temperature of the area of conductive filaments in the crosstalked RRAM device according to the present invention over time. Case 1 and Case 2 curves respectively correspond to the two cases of FIG. 3(a) and FIG. 3(b).

FIG. 8 shows the maximum temperature of the conductive filament region of the crosstalked RRAM device changing with time in the two worst cases shown in FIG. 7. Case 1 and Case 2 correspond to the condition shown in FIGS. 7(a) and 7(b) respectively.

Step 7: Reducing Thermal Crosstalk Effects in Three-Dimensional Integrated Resistive Switching Devices Through the above steps 1, 2, 3, 4, 5, and 6 for the analysis of the thermal effects and thermal crosstalk of the three-dimensional integrated resistive switching memory device, the device structure shown in FIG. 2(a) is used in the present invention, wherein the crossbar array structure with the resistive switching memory cell connected with the diodes via WL/BL (as shown in FIG. 2(a)) can significantly reduce the heat accumulation inside the device and can significantly improve 3D integrated RRAM thermal crosstalk in combination with the following two methods:

One method is to effectively reduce the thermal crosstalk effect by reducing the reset current $I_{reset}$ of the RRAM device.

Figure 9:
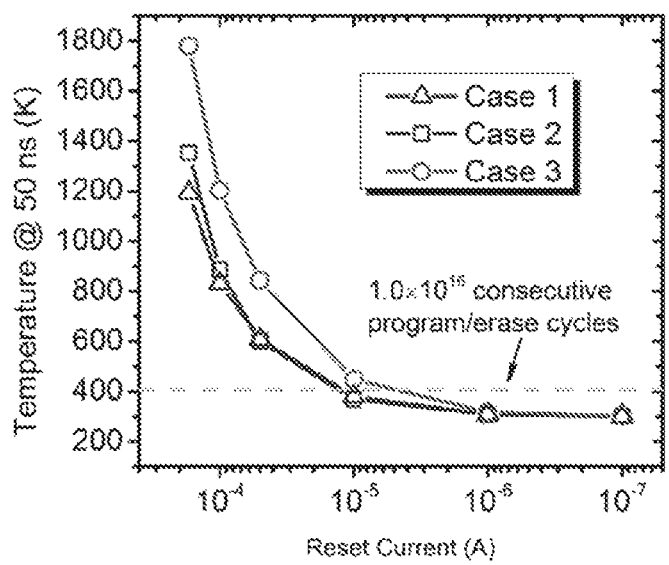
FIG. 9 shows the change of maximum temperature in the crosstalked RRAM device with $I_{reset}$ at t=50 ns calculated according to the present invention.
Figure 10:
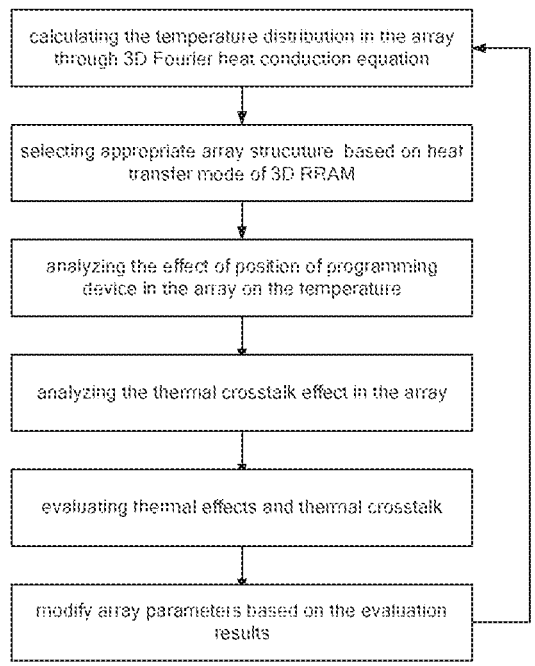
FIG. 10 is a schematic flowchart of a method according to the present invention.

FIG. 9 shows the variation of the maximum temperature of the crosstalked RRAM device with $I_{reset}$ at t=50 ns. When t=50 ns, the maximum temperature of the conductive filaments of the crosstalked RRAM device varies with $I_{reset}$, and the feature size of the selected device is 30 nm in the figure. As $I_{reset}$ decreases from $1.7\times10^{-4}$ A to $1.0\times10^{-4}$ A, the temperature in the crosstalked RRAM device drops significantly. From the evaluation method of step 6, it can be seen that in the case where the crosstalk temperature is 406K, the crosstalked RRAM device can withstand $10^{16}$ continuous program/erase operations without failure (indicated by a dashed line in FIG. 9). $1.0\times10^{16}$ is also the operable number of DRAM type devices in the existing computer system. The corresponding $I_{reset}$ of Case 1 to Case 3 is $1.2\times10^{-5}$ A, $1.2\times10^{-5}$ A 和 $4.7\times10^{-6}$ A respectively, all three are reasonable $I_{reset}$ values for unipolar RRAM devices.

The other method is the use of a cycle-rehabilitate technique.

In order to both further reduce the feature size and ensure the reliability of the device under the influence of thermal crosstalk, this example will use a cycle-rehabilitate technique to overcome the thermal crosstalk—namely after $c_r$ times cycles of RRAM arrays (it should be guaranteed that the resistance value can still distinguish between high and low resistance states in the degraded crosstalked RRAM device after $c_r$ times operations), all of the low resistance state (LRS) devices in the array are erased, and then performed reprogramming operation. With this method, the resistance of the LRS resistive device that is the degraded due to the thermal crosstalk can be rehabilitated to the initial LRS by the reprogramming operation, counterbalancing the influence of the resistance state degradation caused by the thermal crosstalk effect, and furthermore promoting the miniaturization of the RRAM array feature size.

According to the method of the present invention, the influence of the position of the device on the temperature is analyzed according to the heat transfer mode of the 3D RRAM array, the thermal effect and the thermal crosstalk are evaluated, and the appropriate array structure and operating parameters are selected according to the evaluation result, which effectively improves the thermal stability of the device.

Although the invention has been described with reference to one or more exemplary embodiments, those skilled in the art will appreciate that various suitable changes and equivalent arrangements of the device structure or method flow may be made without departing from the scope of the invention. In addition, from the teachings disclosed, many modifications may be made to suit a particular situation or material without departing from the scope of the invention. Therefore, the present invention is not intended to be limited to the specific embodiments disclosed as the best mode for carrying out the present invention, but the disclosed device structure and the manufacturing method thereof will include all the embodiments falling within the scope of the present invention.

The invention claimed is:

1. A method for evaluating the thermal effects of 3D RRAM arrays and reducing thermal crosstalk, the method comprising:
   calculating the temperature distribution in the array through 3D Fourier heat conduction equation;
   selecting a heat transfer mode;
   selecting an appropriate array structure;
   analyzing the effect of position of programming device in the array on the temperature;
   analyzing the thermal crosstalk effect in the array;
   evaluating thermal effects and thermal crosstalk;
   changing the array structure or modifying operating parameters based on the evaluation results to reduce the thermal crosstalk.

2. The method according to claim 1, wherein the 3D Fourier heat conduction equation is $$\nabla k_{th} \nabla T + \sigma |\nabla V|^2 - c\rho \frac{\partial T}{\partial t} = 0 \qquad (1)$$

wherein $k_{th}$ represents thermal conductivity, T represents temperature, c represents heat capacity, $\rho$ represents mass density of the material, t represents time, and $\sigma$ represents electric conductance of material; preferably, the electric conductance of material changes with temperature, as shown in the following formula (2):

$$\sigma = \frac{\sigma_0}{1 + \alpha(T - T_0)} \qquad (2)$$

wherein $\alpha$ represents temperature coefficient of resistance, $\sigma_0$ represents the resistivity at room temperature $T_0$; the word line (WL) or bit line (BL) at the top and bottom of the array has an ideal heat dissipation package structure, the temperatures of top and bottom of the array are kept at room temperature $T_0$ in the calculation, as shown in equation (3):

$$T - T_0 |_{BC} 0. \qquad (3)$$

3. The method according to claim 1, wherein in the heat transfer mode:
   (i) heat is transferred between devices in same layer through the isolating dielectric material, or
   (ii) heat is transferred between RRAM devices in different layers in vertical direction.

4. The method according to claim 1, wherein the array structure is a 3D array of device units, each of which comprises one RRAM and one diode, wherein:
   (i) the RRAM in one unit is connected to the diode in the adjacent unit via a WL/BL, or
   (ii) the diode in one unit is connected to the diode in the adjacent unit via a WL/BL.

5. The method according to claim 2, wherein, the thermal effect of the 3D integrated resistive switching device is analyzed by using the 3D Fourier heat conduction equation based on the physical parameters of conductive filaments of the RRAM device, diodes, and WL/BL, wherein the physical parameters are selected from any one of the following or any combinations thereof: radius, thickness, thermal conductivity, heat capacity, reference conductivity at room temperature, width, reset voltage, and room temperature.

6. The method of claim 1, wherein in the thermal effects and thermal crosstalk in the device are estimated using transient temperature based on the Arrhenius law of the memory device.

7. The method according to claim 1, wherein changing the array structure or modifying operating parameters based on the evaluation results to reduce the thermal crosstalk further comprises: reducing the reset current or adopting a cycle-rehabilitate technique; the cycle-rehabilitate technique comprises after cr times cycles of RRAM arrays, all of the low resistance state devices in the array are erased and then a reprogramming operation is performed; and it is guaranteed that the resistance value can still distinguish between high and low resistance states in the degraded crosstalked RRAM device after cr times operations.

* * * * *